(12) United States Patent
Breton et al.

(10) Patent No.: US 6,471,997 B1
(45) Date of Patent: *Oct. 29, 2002

(54) IRIDACEAE EXTRACT AND COMPOSITIONS CONTAINING IT

(75) Inventors: Lionel Breton, Versailles; Richard Martin, Rochecorbon; Olivier De Lacharriere, Paris, all of (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/709,658

(22) Filed: Sep. 9, 1996

(30) Foreign Application Priority Data

Sep. 7, 1995 (FR) .............................. 95 10487
Sep. 7, 1995 (FR) .............................. 95 10486
Mar. 27, 1996 (FR) .............................. 96 03815

(51) Int. Cl.$^7$ .......................... A61K 35/78; A01N 65/00
(52) U.S. Cl. ...................... 424/725; 424/773; 424/774; 424/779
(58) Field of Search .................... 536/123.1, 123.12, 536/123.13; 424/195.1, 725, 773, 774, 779

(56) References Cited

U.S. PATENT DOCUMENTS

| | | | |
|---|---|---|---|
| 4,963,480 A | | 10/1990 | Belcour et al. |
| 5,716,625 A | | 2/1998 | Hahn et al. |
| 5,795,574 A | * | 8/1998 | Breton et al. ............ 424/195.1 |
| 5,824,320 A | * | 10/1998 | Rouillard et al. .......... 424/401 |
| 5,858,024 A | * | 1/1999 | DeLacharriere et al. ....... 8/408 |
| 5,900,257 A | * | 5/1999 | Breton et al. |
| 6,146,636 A | * | 11/2000 | Breton et al. |
| 6,147,121 A | * | 11/2000 | Breton et al. |
| 6,264,962 B1 | * | 7/2001 | Breton et al. |

FOREIGN PATENT DOCUMENTS

| | | | |
|---|---|---|---|
| JP | 62-61924 A | * | 3/1987 |
| JP | 63196522 A | * | 8/1988 |
| JP | 63216824 A | * | 9/1988 |
| JP | 2142743 A | * | 5/1990 |
| JP | 2-163017 A | * | 6/1990 |
| JP | 4182446 A | * | 6/1992 |
| JP | 4-305518 A | * | 10/1992 |
| JP | 5-4908 A | * | 1/1993 |
| JP | 5221915 A | * | 8/1993 |
| JP | 6-136253 A | * | 5/1994 |
| JP | 06327484 A | * | 11/1994 |
| JP | 07025762 A | * | 1/1995 |
| JP | 7138179 A | * | 5/1995 |
| JP | 7138181 A | * | 5/1995 |
| JP | 07173148 A | * | 7/1995 |
| JP | 07285845 A | * | 10/1995 |
| JP | 8040921 A | * | 2/1996 |
| JP | 8040922 A | * | 2/1996 |
| JP | 08059536 A | * | 3/1996 |
| JP | 08301758 A | * | 11/1996 |
| JP | 09030954 A | * | 2/1997 |
| WO | WO 96/19183 | | 6/1996 |
| WO | WO 96/19228 | | 6/1996 |

OTHER PUBLICATIONS

Seki et al., Phytochemistry, vol. 38, No. 4, pp. 965–973, (1995).*
Database WPI, Section CH, Week 9601, Derwent Publications Ltd., London, GB, Class D21, AN 96–006882, XP002004988 & JP–A–07 285 845 (Pola Chem Ind Inc), Oct. 31, 1995.
Database WPI, Section CH, Week 9536, Derwent Publications Ltd., London, GB, Glass B02, AN 95–272884, XP002004989 & JP–A–07 173 148 (Kikkoman Corp), Jul. 11, 1995.
Gabriel Garnier Et Al.: "Ressources Medicinals De La Flore Francaise" 1961, Vigot Freres, Paris, XP002004987, pp. 277–285.

* cited by examiner

Primary Examiner—James O. Wilson
(74) Attorney, Agent, or Firm—Burns, Doane, Swecker & Mathis, L.L.P.

(57) ABSTRACT

The subject of the present invention, in its most general aspect, is an extract of cells of at least one plant of the Iridaceae family, the said plant being obtained by in vitro culture. The subject of the invention is also compositions containing an extract of cells of at least one plant of the Iridaceae family, the use of the said extracts as antagonist of CGRP and/or of substance P and a process of cosmetic treatment involving one of the said compositions.

55 Claims, No Drawings

IRIDACEAE EXTRACT AND COMPOSITIONS CONTAINING IT

BACKGROUND OF THE INVENTION

TECHNICAL FIELD OF THE INVENTION

The subject of the present invention, in its most general aspect, is an extract of cells of at least one plant of the Iridaceae family, the said plant being obtained by in vitro culture. The subject of the invention is also compositions containing an extract of cells of at least one plant of the Iridaceae family, the use of the said extracts as antagonists of CGRP and/or of substance P and a process of cosmetic treatment involving one of the said compositions.

To the knowledge of the applicant, up until now, no extract of cells of at least one plant of the Iridaceae family has been described, the said plant being obtained by in vitro culture.

The applicant having demonstrated, after long studies, specific properties of such an extract, it proposes, as novel product, an extract of cells of at least one plant of the Iridaceae family, the said plant being obtained by in vitro culture.

In the text which follows, the term "Iridaceae cells" should be understood as "cells of at least one plant of the Iridaceae family." Likewise, the term "Iridaceae extract" should be understood as "extract of Iridaceae cells" and therefore as "extract of cells of at least one plant of the Iridaceae family."

The extract of cells of at least one plant of the Iridaceae family may be an extract prepared from any plant material derived from the Iridaceae family, the said material having been obtained by in vitro culture.

The selection pressure imposed by the physicochemical conditions during the growth of plant cells in vitro makes it possible to obtain a plant material which is standardized and available throughout the year, contrary to the plants obtained by in vitro culture.

In vitro culture is understood to mean the range of techniques known to a person skilled in the art which makes it possible artificially to obtain a plant or a portion of a plant.

Thus, for example, according to the invention, the extract may be an extract of an organ or even of cells of an organ of at least one Iridaceae obtained by in vitro culture (root, stem, leaf) or alternatively an extract of undifferentiated cells of at least one Iridaceae.

Preferably, an extract obtained from undifferentiated cells obtained by in vitro culture is used.

Undifferentiated plant cells is understood to mean any plant cell exhibiting none of the characters of a specific specialization and capable of living by itself and not in dependence on other cells. These undifferentiated plant cells may be capable, under the effect of an induction, of any differentiation consistent with their genome.

According to the chosen method of culture, and in particular according to the chosen culture medium, it is possible to obtain, from the same explant, undifferentiated plant cells having different characters.

The Iridaceae (or Irid) family comprises about 750 species.

The plants of the Iridaceae family are used especially for their aromatic and ornamental properties.

Among the Iridaceae genera which can be used according to the invention, there may be mentioned by way of example the genera Romulea, Crocus, Iris, Gladiolus, Sisyrinchium or alternatively Hermodactylus.

As plant material which can be used, there may be mentioned that obtained from *Iris germanica, Iris florentina, Iris pallida, Crocus versicolor, Romulea bulbucodium* or alternatively *Gladiolus Communis*.

More particularly, according to the invention, plant material derived from the genus Iris, more particularly from *Iris pallida*, is used.

Any method of extraction known to persons skilled in the art may be used according to the invention.

There may be mentioned in particular alcoholic, especially ethanolic, extracts and aqueous-alcoholic extracts.

There may also be used an extract prepared by the method described in French Patent Application No. 95-02379.

Thus, in a first step, the plant material is ground in an aqueous solution at cold temperature, in a second step, the particles in suspension are removed from the aqueous solution derived from the first step, and in a third step, the aqueous solution derived from the second step is sterilized. This aqueous solution corresponds to the extract.

Moreover, the first step may be advantageously replaced by a simple operation of freezing the plant tissues (for example at $-20°$ C.), followed by an aqueous extraction comprising the second and third steps described above.

An example of extract preparation which can be used according to the invention is given, furthermore, in the examples.

The subject of the invention is also a cosmetic or pharmaceutical composition comprising, as active ingredient, in a cosmetically or pharmaceutically acceptable medium, at least one extract of plant material of at least one Iridaceae as defined above.

Active ingredient is understood to mean any molecule or extract capable of modifying or modulating the function of at least one given biological system.

There are, in mammals, polypeptides belonging to the family of tachykinins which induce rapid contractions on the smooth muscle fibres. Among the compounds of this family, there may be mentioned b-neurokinin, a-neurokinin and substance P.

Substance P is a polypeptide chemical component (undecapeptide), produced and released by a nerve ending. The location of substance P is specific to the neurons, both in the central nervous system and in the organs at the periphery. Thus, numerous organs or tissues receive afferences of substance P-bearing neurons; these are especially the salivary glands, the stomach, the pancreas, the intestine (in the latter, the distribution of substance P is superposed on the intrinsic Meissner's and Auerbach's nerve plexus), the cardiovascular system, the thyroid gland, the skin, the iris and the ciliary bodies, the bladder and obviously the central and peripheral nervous systems.

By virtue of the ubiquitous distribution of substance P, numerous disorders are associated with an excessive synthesis and/or release of substance P.

Substance P is involved especially in the transmission of pain and in diseases of the central nervous system (for example anxiety, psychoses, neuropathies, neurodegenerative disorders of the type comprising senile dementia of Alzheimer, dementia of AIDs sufferers, Parkinson's disease, Down's syndrome, Korsakoff's syndrome, multiple sclerosis, schizophrenia), in respiratory diseases (such as for example bronchopneumonia) and inflammatory diseases (such as for example rheumatoid arthritis), in allergic syndromes (such as for example asthma, allergic rhinitis, allergic pharyngitis, urticaria, eczematous dermatitis), in gastrointestinal diseases (such as for example ulcers, colitis, Crohn's disease), in skin disorders (such as for example psoriasis, pruriginous diseases, herpes, photodermatosis, atopic dermatitis, contact dermatitis, lichen, prurigo, pruritus, erythema, in particular solar erythema, insect bites), in fibrosis and other collagen maturation disorders (such as for example scleroderma), in cardiovascular disorders, vasospastic disorders (such as for example migraine, Reynaud's disease), in immunological disorders, in disorders of the urinary tract (such as for example incontinence, cystitis), in rheumatic diseases, in some dermatological diseases (such as eczema) and in ophthalmological conditions (such as for example conjunctivitis, uveitis, ocular pruritus, ocular pain, irritations).

The use of a substance P antagonist is one of the therapeutic alternatives which are effective in all the abovementioned conditions.

Substance P antagonist is understood to mean any compound capable of inhibiting partially, or even completely, the biological effect of substance P.

In particular, for a substance to be recognized as a substance P antagonist, it should induce a coherent pharmacological response (including or otherwise its attachment to the substance P receptor) especially in one of the following tests:

the antagonist substance should reduce the extravasation of plasma across the vascular wall induced by capsaicin or by an antidromic nervous stimulation, or alternatively the antagonist substance should cause inhibition of the contraction of the smooth muscles induced by the administration of substance P.

Up until now, substance P antagonists have been used to treat the disorders indicated above. To this end, reference may be made to the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808 and WO-A-93/01165.

However, none of the above documents envisages or suggests that an extract of at least one Iridaceae can have a substance P-antagonizing activity as defined above and therefore can be especially used to treat the disorders indicated above.

The applicant has discovered that an extract of at least one Iridaceae corresponds to the characteristics defined as characterizing a substance P antagonist and can therefore be used as a substance P antagonist.

CGRP is a polypeptide chemical component produced and released by a nerve ending.

The location of CGRP is specific to the sensitive nerve fibres (C fibres). Thus, numerous organs or tissues receive afferences of CGRP-bearing neurons; these are especially the salivary glands, the stomach, the pancreas, the intestine, the cardiovascular system, the thyroid gland and the skin.

By virtue of the ubiquitous distribution of CGRP, numerous pathologies are associated with an excessive synthesis and/or release of CGRP.

These are especially respiratory and inflammatory diseases, allergic diseases, skin disorders, especially dermatological conditions such as eczema, prurigo, rosacea.

The use of a CGRP antagonist is one of the alternative treatments which are effective in all the abovementioned conditions.

CGRP antagonist is understood to mean any compound capable of inhibiting partially or even completely the biological effect of CGRP.

In particular, for a substance to be recognized as a CGRP antagonist, it should induce a coherent, pharmacological response (including or otherwise its attachment to the CGRP receptor) especially in one of the following tests:

the antagonist substance should reduce the vasodilation induced by capsaicin and/or by an antidromic electrical stimulation (applied to an afferent nerve) and/or the antagonist substance should cause inhibition of the release of CGRP by the sensitive nerve fibres and/or the antagonist substance should cause inhibition of the contraction of the smooth muscle of the vas deferens induced by CGRP.

Among the known CGRP antagonists, there may be mentioned for example CGRP 8–37 (sequence of amino acids 8 to 37 of the N-terminal part of CGRP) or alternatively the anti-CGRP antibodies.

Up until now, it has not been envisaged or even suggested that an extract of at least one Iridaceae can have a CGRP-antagonizing activity.

The applicant has discovered that an extract of at least one Iridaceae corresponds to the characteristics defined as characterizing a CGRP antagonist and can therefore be used as a CGRP antagonist.

There have been seen elsewhere in the text examples of linked disorders associated with an excessive synthesis and/or release of substance P or with an excessive synthesis and/or release of CGRP.

Thus, the subject of the invention is therefore a cosmetic or pharmaceutical composition comprising, as active ingredient, in a cosmetically or pharmaceutically acceptable medium, at least one extract of plant material of at least one Iridaceae intended to treat disorders of the central nervous system, respiratory disorders, allergic syndromes, inflammation, pain, gastrointestinal disorders, skin disorders, fibrosis, collagen maturation disorders, cardiovascular disorders, vasospastic disorders, immunological disorders and/or disorders of the urinary tract.

In the area of skin disorders, it is known that some skins are more sensitive than others. However, the symptoms of sensitive skins were, up until now, poorly characterized and the problem of these skins was, as a result, poorly defined; no one knew exactly the process involved in the sensitization of the skin. Some thought that a sensitive skin was a skin which reacted to cosmetic products, others that it was a skin which reacted to several external factors, not necessarily linked to cosmetic products. Sensitive skin was also synonymous with allergic skin.

Tests have been developed to understand sensitive skins, for example tests with lactic acid and DMSO which are known to be irritant substances: see for example the article by K. Lammintausta et al., Dermatoses, 1988, 36, pages 45–49; and the article by T. Agner and J. Serup, Clinical and Experimental Dermatology, 1989, 14, pages 214–217.

Because of the lack of knowledge about the characteristics of sensitive skins, it was, up until now, very difficult or even impossible to treat them. In fact, they were treated indirectly, for example by limiting, in the cosmetic or dermatological compositions, the use of products with an irritant characteristic, such as surfactants, preservatives, perfumes as well as the use of some cosmetic or dermatological active agents.

After numerous clinical tests, the applicant has been able to determine the symptoms linked to sensitive skins. These symptoms are in particular subjective signs, which are essentially dysaesthetic sensations. Dysaesthetic sensations is understood to mean more or less painful sensations felt in a skin area such as prickling, formication, itching, pruritus, burn, inflammation, discomfort, stabbing pain. The symptoms linked to the skin may also be microvascular manifestations of the skin tissue such as erythemas.

The applicant has been able to show, in addition, that a sensitive skin was not an allergic skin. Indeed, an allergic skin is a skin which reacts to an external agent, an allergen, which triggers an allergic reaction. It is an immunological process which occurs only when an allergen is present and which only affects sensitized subjects. The essential characteristic of the sensitive skin is, according to the applicant, on the contrary, a mechanism of response to external factors, which may affect any individual, even though the individuals with so-called sensitive skin react thereto more quickly than others. This mechanism is not immunological; it is aspecific.

The applicant has found that sensitive skins could be separated into two main clinical forms, the irritable and/or reactive skins, and the intolerant skins.

An irritable and/or reactive skin is a skin which reacts by pruritus, that is to say by itching, or by prickling, to various factors such as the environment, emotions, food, wind, rubbing, razor, soap, surfactants, hard water with a high chalk concentration, temperature variations or wool. In general, these signs are associated with a dry skin with or without dartre, or with a skin exhibiting an erythema.

An intolerant skin is a skin which reacts by sensations of inflammation, stabbing pain, formication and/or blotches, to various factors such as the environment, emotions, food and some cosmetic products. In general, these signs are also associated with a hyperseborrhoeic skin or with a skin with acne, with or without dartre, and with an erythema.

"Sensitive" scalps have a more univocal clinical semiology: the sensations of pruritus and/or of prickling and/or of inflammation are essentially triggered by local factors such as rubbing, soap, surfactants, hard water with a high chalk concentration, shampoos or lotions. These sensations are also sometimes triggered by factors such as the environment, emotions and/or food. An erythema and a hyperseborrhoea of the scalp, as well as a dandruff condition, are frequently associated with the above signs.

Furthermore, in some anatomical regions such as the large skin-folds (inguinal, genital, axillary, popliteal, anal or submammary regions, skin-fold of the elbow) and the feet, the sensitive skin results in pruriginous sensations and/or dysaesthetic sensations (inflammation, prickling) linked in particular to sweat, rubbing, wool, surfactants, some cosmetic preparations, hard water with a high chalk concentration and/or temperature variations.

To determine if a skin is sensitive or not, the applicant also developed a test. Indeed, after having carried out a large number of tests with the aim of defining a sensitive skin, it found, surprisingly, that there was a link between persons with sensitive skin and those who reacted to a topical application of capsaicin.

The capsaicin test consists in applying, over about 4 cm$^2$ of skin, 0.05 ml of a cream comprising 0.075% capsaicin and in noting the appearance of subjective signs caused by this application, such as prickling, burns and itching. In subjects with sensitive skins, these signs appear between 3 to 20 minutes after the application and are followed by the appearance of an erythema which starts at the periphery of the area of application.

Up until now, capsaicin was used as a medicinal product, in particular to treat zona pains. Capsaicin causes a release of the neuropeptides, and in particular of CGRP and tachykinins which are derived from the nerve endings of the epidermis and of the dermis. The applicant observed that the physiopathological pattern common to all the conditions of sensitive skins was linked to a high capacity to release neuropeptides and tachykinins and more particularly CGRP and substance P in the skin. The dysaesthetic manifestations which are caused by their release are termed "neurogenic."

No one had, up until now, established a link between CGRP and sensitive skin and/or substance P and sensitive skin. The clinical signs of sensitive skin are essentially subjective: prickling, formication, pruritus, stabbing pain, inflammation, and they are sometimes combined with erythemas. These signs are due to aspecific external factors. The symptoms appear to be essentially restricted to the face, the neck and the scalp, but may also appear on the whole body.

Thus, the applicant has discovered that one of the essential characteristics of sensitive skins is linked to the release of CGRP and/or of substance P and therefore that the use of CGRP antagonists and/or of a substance P antagonist, including in particular an extract of plant material of at least one Iridaceae, can make it possible to obtain a preventive and/or curative effect on sensitive skins.

Thus, the subject of the invention is a cosmetic or pharmaceutical composition intended to treat sensitive skins, characterized in that it comprises, in a cosmetically or pharmaceutically acceptable medium, as active ingredient, at least one extract of plant material as defined above.

To treat sensitive skins, the applicant therefore envisaged using CGRP antagonists and/or substance P antagonists. It has indeed observed, surprisingly, that the incorporation of a CGRP antagonist and/or a substance P antagonist into a composition intended for a topical use makes it possible to avoid skin irritation and/or dysaesthetic sensations and/or pruritus of the skin and/or the mucous membranes and/or erythema and/or dartre and/or sensations of inflammation.

The subject of the invention is therefore a cosmetic or pharmaceutical composition intended to treat skin irritation and/or dysaesthetic sensations and/or pruritus of the skin and/or of the mucous membranes and/or erythema and/or dartre and/or sensations of inflammation.

Advantageously, according to the invention, at least one extract of at least one Iridaceae may be combined with products with an irritant effect which are commonly used in the cosmetic or pharmaceutical field, which products are sometimes cosmetic or pharmaceutical active agents. The presence of a substance P antagonist in the form of at least one extract of at least one Iridaceae in a cosmetic or pharmaceutical composition comprising a product having an irritant effect makes it possible to attenuate substantially or even eliminate this irritant effect.

This makes it possible, in addition, to increase the quantity of active ingredient with an irritant effect relative to the quantity of active ingredient normally used, for the purpose of an enhanced efficacy.

The invention relates more particularly to a cosmetic or pharmaceutical composition, characterized in that it comprises, in a cosmetically or pharmaceutically acceptable medium, at least one product with an irritant effect and at least one extract of at least one Iridaceae.

As products with an irritant effect, there may be mentioned, for example, surfactants (ionic or nonionic), preservatives, organic solvents or active agents such as a-hydroxy acids (citric, malic, glycolic, tartaric, mandelic or lactic acid), b-hydroxy acids (salicylic acid and its derivatives), a-keto acids, b-keto acids, retinoids (retinol, retinal, retinoic acid), anthralins (dioxyanthranol), anthranoids, peroxides (especially benzoyl peroxides), minoxidil, lithium salts, antimetabolites, vitamin D and its derivatives, hair dyes or colorants (para-phenylenediamine and its derivatives, aminophenols), perfuming alcoholic solutions (perfumes, toilet waters, aftershave, deodorants), antiperspirants (some aluminium salts), depilatory or permanent-waving active agents (thiols), depigmenting active agents (hydroquinone).

The use of a substance P antagonist makes it possible, in particular, to multiply 2- to 10-fold the quantity of active ingredient with an irritant effect relative to the prior state of the art, without feeling all the discomforts mentioned above. Thus, hydroxy acids may be used up to 50% of the weight of the composition and retinoids up to 5%, by substantially reducing their irritant character.

Preferably, the extract of at least one Iridaceae is an extract as described above in the text.

It is known, furthermore, that numerous phenomena of intolerance exist at the level of the skin, of which the symptoms are in particular subjective signs which are essentially dysaesthetic sensations. Dysaesthetic sensations is understood to mean more or less painful sensations felt in a skin region such as prickling, formication, itching or pruritus, burns, inflammation, discomfort, stabbing pain and the like.

These phenomena may be the consequence of multiple events, of which the most common will be described as irritation or inflammation, but some of which will be due to physiological causes, like sensitive skins, or even pathological causes like, for example, allergy.

However, the sensitive skin may also react by sensations of inflammation, stabbing pain, formication and/or blotches, to various factors such as the environment, emotions or food. In general, these signs are associated with a hyperseborrhoeic skin or a skin with acne, with or without dartres. Here also, these signs are often assocaited with an erythema.

These phenomena can be generalized to the whole body, but most often, they may have well-defined locations such as for example the scalp, the face, the skin folds and the like.

The range of these intolerance phenomena is always linked to a conventional inflammatory process, and more particularly to an inflammatory reaction of the neurogenic type since it involves cutaneous nerve fibres.

An allergic skin is a skin which reacts to an external agent, an allergen, which triggers an allergic reaction. It is therefore a specifically immunological process which occurs only when an allergen is present and which affects only sensitized subjects. On the other hand, the final product of an allergic reaction also results in an acute inflammatory reaction generally associated with an oedema.

Regardless of the phenomenon envisaged there is a feature common to all these mechanisms which results in an inflammatory reaction, of which the terminal facet can be measured by the release, by the mast cells of the skin, of at least one inflammation mediator such as histamine, serotonin, heparin, leukotrienes, prostaglandins, cytokines, nitrogen monoxide or reactive oxygen-containing species.

In some cases, such as for example sensitive skins, the entire mechanism is also under the control of the sensitive nerve endings which release neuropeptides, especially substance P and CGRP.

The desired aim of the present invention is to obtain the widest possible beneficial effect in the treatment of all these skin conditions and therefore to propose a composition which acts on several components of these conditions.

Thus, according to another aspect, the subject of the present invention is a cosmetic or pharmaceutical composition, characterized in that it comprises, in a cosmetically or pharmaceutically acceptable medium, an extract of at least one Iridaceae and a compound reducing the synthesis, release and/or the activity of at least one inflammation mediator.

Preferably, the extract of at least one Iridaceae is an extract as described above in the text.

Among the steroidal anti-inflammatory agents, there may be mentioned, by way of example, hydrocortisone, betamethasone valerate or clobetasol propionate.

Non-steroidal anti-inflammatory agents is understood here to mean anti-inflammatory agents as described by Schorderet and Dayer in Pharmacologie, "Des concepts fondamentaux aux applications thérapeutiques" (Concepts fundamental to therapeutic applications), 1992, Chapter 37, pages 541–561, 2nd edition, Frison-Roche/Slatkine editors. They are arylcarboxylic acids, such as the derivatives of salicylic acid or the derivatives of anthranilic acid, arylalkanoic acids, such as arylacetic and heteroarylacetic acids or arylpropionic acids, enolic acids, such as the derivatives of pyrazolone or oxicams, non-acidic derivatives, such as for example bufexamac (Merck Index, 11th edition (M.I.) 1462), benzydamine (M.I. 1136), epirizole (M.I. 3572), fluproquazone (M.I. 4120) or tiaramide (M.I. 9356).

Preferably, the composition according to the invention comprises a compound reducing the synthesis, release and/or activity of at least one skin inflammation mediator in combination with the extract of at least one Iridaceae.

The composition reducing the synthesis, release and/or activity of at least one inflammation mediator is preferably chosen from substance P and/or CGRP antagonists, NO-synthase inhibitors, bradykinin antagonists, antagonists of cytokines, histamine antagonists, antagonists of type a tumour necrosis factor (TNFa).

Preferably, receptor antagonists are used.

For example, according to the invention, it is possible to use one or more substance P antagonists chosen from peptides, nonpeptide compounds such as those comprising at least one heterocycle, nitrogen-containing compounds comprising at least one benzene ring, salts of monovalent, divalent and trivalent cations, thermal waters, and mixtures thereof.

Sendide and Spantide II may be used in the invention, for example, as substance P-antagonizing peptide.

Sendide corresponds to the formula:

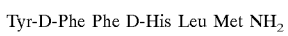

in which:

Tyr represents tyrosine,

D-Phe represents D-phenylalanine

Phe represents phenylalanine

D-His represents D-histidine,

Leu represents leucine

Met represents methionine.

Spantide II corresponds to the formula (SEQ ID NO.:1):

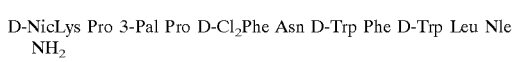

in which:

D-NicLys represents D-lysine nicotinate,

Pro represents proline,

3-Pal represents 3-pyridyl-alanine,

D-Cl$_2$Phe represents D-dichlorophenylalanine,

Asn represents asparagine,

D-Trp represents D-tryptophan

Phe represents phenylalanine,

Leu represents leucine,

Nle represents norleucine.

It is also possible to use in the invention, as substance P-antagonizing peptide, the peptides described in the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide substance P antagonists which can be used in the invention are especially compounds comprising a heteroatom linked directly or indirectly to a benzene ring or contained in a heterocycle. In particular, this heteroatom is an oxygen, nitrogen or sulphur atom.

As heterocyclic compound, there may in particular be used in the invention those described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116.

In particular, the compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

As other heterocyclic compounds, there may be mentioned oxygen-containing or sulphur-containing heterocyclic compounds such as furan derivatives, benzofuran derivatives, thiophene derivatives, benzothiophene derivatives, optionally comprising nitrogen-containing substituents, such as the heterocyclic compounds described in the documents U.S. Pat. No. 4,931,459, U.S. Pat. No. 4,910,317 and EP-A-299457, and more especially the alkoxy- and/or aryloxy-tetrazolyl-benzofuran-carboxamides and alkoxy- and/or aryloxy-tetrazolyl-benzothiophene-carboxamides.

As compounds comprising a nitrogen atom linked directly or indirectly to a benzene ring, there may be mentioned those described in the following documents: EP-A-522808 and WO-A-93/01165 and WO-A-93/10073.

The salts of cations which can be used in the invention are especially the salts of strontium, magnesium, lanthanides of atomic number ranging from 57 to 71, cobalt, nickel, manganese, barium, yttrium, copper, tin, rubidium, lithium and zinc.

These salts may be for example carbonates, salicylates, bicarbonates, sulphates, glycerophosphates, borates, chlorides, nitrates, acetates, hydroxides, persulphates as well as salts of a-hydroxy acids (citrates, tartrates, lactates, malates) or of fruit acids, or alternatively salts of amino acids (aspartate, arginate, glycocholate, fumarate) or salts of fatty acids (palmitate, oleate, caseinate, behenate). Preferably, the salt is chosen from strontium, manganese, yttrium or magnesium nitrate, strontium, manganese, yttrium or magnesium borate, strontium, manganese or magnesium chloride, magnesium, manganese or strontium sulphate. Still more preferably, these salts are strontium chloride or nitrate.

Among the thermal waters which can be used according to the invention, there may be mentioned more particularly the thermal waters of the Vichy basin, such as those derived from the Célestins, Chomel, Grande-Grille, Hôpital, Lucas and Parc springs. Preferably, according to the invention, water from the Lucas spring is used.

The substance P antagonists may be used alone or in the form of a mixture.

CGRP antagonist is understood to mean any compound capable of inhibiting partially or even completely the biological effect of CGRP.

In particular, for a substance to be recognized as a CGRP antagonist, it should induce a coherent pharmacological response (including or otherwise its attachment to the CGRP receptor) especially in one of the following tests:

the antagonist substance should reduce the vasodilation induced by capsaicin and/or by an antidromic electrical stimulation (applied to an afferent nerve) and/or the antagonist substance should cause inhibition of the release of CGRP by the sensitive nerve fibres and/or the antagonist substance should reduse inhibition of the contraction of the smooth muscle of the vas deferens induced by CGRP.

Among the known CGRP antagonists, there may be mentioned for example CGRP 8–37 (sequence of amino acids 8 to 37 of the N-terminal part of CGRP) or alternatively the anti-CGRP antibodies.

The CGRP antagonists may be used alone or in the form of a mixture.

The term NO-synthase in fact covers a family of enzymes which bring about specifically the enzymatic catalysis of L-arginine to citrulline, during which catalysis a gaseous mediator with multiple functions, nitrogen monoxide or NO, is produced. Nitrogen monoxide has, by virtue of its structure, an additional electron which makes it extremely chemically reactive. It is a well-known fact that such compounds are harmful and efforts are made to limit their production as much as possible. Consequently, in the case of nitrogen monoxide, inhibitors of NO-synthase have been widely studied.

Thus, according to the invention, the inhibitors of NO-synthase are products which make it possible in situ, in man, to inhibit partially or even completely the synthesis of nitrogen monoxide (NO).

These are therefore compounds chosen from the compounds inhibiting the synthesis and/or accelerating the catabolism of NO-synthase, the compounds neutralizing NO-synthase or the compounds involved in decreasing the signal transduced by NO-synthase.

Thus, the inhibitor of NO-synthase may be chosen from optionally modified synthetic or natural peptides, synthetic or natural chemical molecules, antisense nucleic acids, ribozymes, anti-NO-synthase antibodies.

Among these inhibitors of NO-synthase, there may be mentioned especially $N^G$-monomethyl-L-arginine (L-NMMA), $N^G$-nitro-L-arginine, the methylated ester of $N^G$-nitro-L-arginine, diphenyleneiodonium chloride, 7-nitroindazole, N(5)-(1-iminoethyl)-L-ornithine, $N^G$,$N^G$-dimethyl-L-arginine, $N^G$,$N^G$-dimethylarginine, 2-(4-carboxyphenyl)-4,4,5,5-tetramethylimidazoline-1-oxy-3-oxide, aminoguanidine, canavanine, ebselen and type a melanocyte-stimulating hormone.

Among the inhibitors of NO-synthase, $N^G$-monomethyl-L-arginine and the type a melanocyte-stimulating hormone are preferably used. The inhibitors of NO-synthase may be used alone or in the form of a mixture.

Bradykinin is a peptide of plasma origin which is released from a kininogenic precursor by a plasma protease called Kallikrein (EC 3.4.21.24). This nanopeptide is one of the key mediators of inflammation and has mitogenic properties. The receptors for this kinin can be separated into two principal subtypes B1 and B2. Bradykinin acts especially on the B2 receptor and causes stimulation of numerous systems of production of second messengers, including the hydrolysis of inositol phosphates, the metabolism of arachidonic acid, the phosphorylation of tyrosine residues as well as the depolarization or the hyperpolarization of the cell membrane.

The activation of some receptors causes the activation of phospholipase C and therefore the production of inositol 1,4,5-triphosphate (IP3) and of diacylglycerol (DAG). IP3 is known to cause the release of calcium from the intracellular storage sites in the cells including the keratinocyte. Calcium, described as an activator and regulator of numerous enzymes (proteases, phospholipases), plays a major role in the regulation of the differentiation and the proliferation of the keratinocyte.

Bradykinin antagonist is understood to mean any compound capable of partially or even completely inhibiting the biological effect of bradykinin.

In particular, for a substance to be recognized as a bradykinin antagonist, it should induce a coherent pharmacological response including or otherwise its attachment to the bradykinin receptor.

Thus, entering into this definition is any compound which may interfere with the effects of bradykinin by its attachment to the receptor for the latter (B1 or B2) and/or any compound which, independently of the attachment to the receptor(s), induces by any mechanism an effect which is the opposite of that known for bradykinin (for example interfering with the synthesis of bradykinin).

Among the bradykinin antagonists, there are preferably used compounds inhibiting the synthesis and/or accelerating the catabolism of bradykinin, compounds neutralizing bradykinin, compounds blocking the bradykinin receptors such as those which interfere with the effects of bradykinin by their attachment to the receptor for the latter (B1 or B2), compounds inhibiting the synthesis of the receptors for bradykinin or compounds which play a role in decreasing the signal transduced by bradykinin. These compounds may be of natural or synthetic origin.

Among the bradykinin antagonists, there may be mentioned more particularly optionally modified synthetic or natural peptides such as D-Arg, [Hyp3, D-Phe7]-bradykinin (NPC567), [Thi 5, 8, D-Phe7]-bradykinin, D-Arg, [Hyp3, Thi5, 8, D-Phe7]-bradykinin, N-a-adamantaneacetyl-D-Arg, [Hyp3, Thi5,8, D-Phe7]-bradykinin, des-Arg9, [Leu8]-bradykinin (all sold by the company Sigma) or alternatively compounds mentioned in the patents WO 95/08566, WO 95/07294, EP 0623350, EP 0622361, WO 94/11021, EP 0596406, WO 94/06453, WO 94/09001, EP 0578521, EP 0564972, EP 0552106, WO 93/11789, U.S. Pat. No. 5,216, 165, U.S. Pat. No. 5,212,182, WO 92/17201, EP 0496369, EP 0472220, EP 0455133, WO 91/09055, WO 91/02746, EP 0413277, EP 0370453, EP 0359310, WO 90/03980, WO 89/09231, WO 89/09230, WO 89/01780, EP 0334244, EP 0596406, WO 86/07263 or P-guanidobenzoyl, [Hyp3, Thi5, D-Tic7, Oic8]-bradykinin (S 16118) (Feletou M & al., Pharmacol. Exp. Ther., June 1995, 273, 1078–84), D-Arg, [Hyp3, Thi5, D-Tic7, Oic8]-bradykinin (HOE 140) Feletou M & al., Eur. J. Pharmacol, 1995, 274, 57–64), D-Arg, [Hyp3, D-Hype (trans-propyl)7 Oic8]-bradykinin (NPC 17731) (Herzig M. C. S. and Leeb-Lundberg L. M. F., J. Biol. Chem. 1995, 270, 20591–20598) or those mentioned in Bradykinin Antagonists: development and applications (Stewart J. M., Biopolymers, 1995, 37, 143–155), or alternatively synthetic or natural chemical molecules such as for example those described in Salvino et al., J. Med. Chem., 1993, 36, 2583–2584.

It is also possible to use, according to the invention, antisense nucleic acids or ribozymes whose role is to inhibit selectively the synthesis of bradykinin. These antisense nucleic acids are known to persons skilled in the art. They may act in various ways on the DNA or messenger RNA coding for bradykinin, especially by blocking the attachment or the progression of the ribosomes along the messenger RNA, by cleaving the messenger RNA with RNase H, or by preventing the transport of messenger RNA from the nucleus to the cytoplasm or alternatively by preventing the maturation of the messenger RNA.

It is also possible to use, according to the invention, anti-bradykinin antibodies or soluble receptors for bradykinin, anti-bradykinin receptor antibodies or antagonists of bradykinin receptors.

Preferably, according to the invention, a compound is used which interferes with the effects of bradykinin by its attachment to the receptor for the latter (B1 or B2), preferably to the B2 receptor.

Still more preferably, there is used according to the invention a bradykinin antagonist chosen from:

D-Arg, [Hyp3, D-Phe7]-bradykinin (NPC567),

[Thi 5, 8, D-Phe7]-bradykinin, D-Arg, [Hyp3, Thi5,8, D-Phe7]-bradykinin,

N-a-adamantaneacetyl-D-Arg, [Hyp3, Thi5,8, D-Phe7]-bradykinin, des-Arg9, [Leu8]-bradykinin, P-guanidobenzoyl, [Hyp3, Thi5, D-Tic7, Oic8]-bradykinin (S 16118), D-Arg, [Hyp3, Thi5, D-Tic7, Oic8]-bradykinin (HOE 140), D-Arg, [Hyp3, D-Hype (trans-propyl)7 Oic8]-bradykinin (NPC 17731)

The modified peptide preferably used according to the invention is D-Arg, [Hyp3, Thi5, D-Tic7, Oic8]-bradykinin (HOE 140).

The bradykinin antagonists may be used alone or in the form of a mixture.

It is known, furthermore, that the substance P released by the sensitive epidermal endings induces a cascade of biochemical events, of which the first steps are situated at the level of the mastocytes. The attachment of substance P to the mastocyte receptors induces a release of numerous proinflammatory mediators, among which are histamine, cytokines such as interleukin-1 (IL-1), interleukin-6 (IL-6), interleukin-8 (IL-8) and type a tumour necrosis factor (Tumour Necrosis Factor a (TNF-a)).

Antagonists of histamine, cytokines and/or TNF-a is understood to mean any substance capable of inhibiting the release and/or the synthesis and/or the receptor attachment of histamine, cytokines and/or TNF-a respectively.

The antagonists inhibiting the receptor attachment of histamine are agents specific for the type 1 receptor for histamine (H1).

For a substance to be recognized as a receptor antagonist of histamine, cytokines or TNF-a, it should correspond to one of the following characteristics:

have an affinity for the receptors specific for these compounds;

have a histamine, cytokine or TNF-a receptor antagonist pharmacological activity, that is to say induce a coherent pharmacological response in one of the following tests:

for the receptor antagonists of histamine: inhibition of the contraction of the smooth muscles which is induced by the administration of histamine;

for the receptor antagonists of cytokines; inhibition of adhesion of macrophages which is induced by the cytokines on endothelial cells or inhibition of the release of superoxide anions which is induced by the cytokines on the neutrophils;

for the receptor antagonists of TNF-a: inhibition of the adhesion of macrophages which is induced by TNF-a on the endothelial cells or inhibition of the release of superoxide anions which is induced by TNF-a on the neutrophils or inhibition of the mitogenic activity of TNF-a on the fibroblasts of the dermis.

For a substance to be recognized as an antagonist of the release and/or synthesis of histamine, cytokines and TNF-a, it should correspond to one of the following characteristics:

inhibition of the release of histamine by mastocytes stimulated by the compound 48/80 or stimulated by a calcium ionophore (A23 187)

inhibition of the release of cytokines or TNF-a by monocytes (U937 cells) differentiated by a phorbol ester (PMA).

The receptor antagonists of histamine H1 which can be used in the invention are those conventionally used in the treatments of allergic and anaphylactic conditions as well as those for combating travelling sickness. These compounds may be for example diethylenediamine derivatives such as cinnarizine or cyclizine; aminopropane derivatives such as dexchlorpheniramine, triprolidine; phenothiazine derivatives such as promethazine, alimemazine, as well as the compounds mentioned on pages 116 to 118 of the book Joseph R. Prous, The Year's Drug News, Therapeutic Targets, 1994 edition, Prous Science Publishers such as cetirizine-HCl, ebastine, loratadine, setastine-HCl.

The inhibitors of histamine release are especially oxygen-containing or sulphur-containing heterocyclic compounds such as furan derivatives, benzofuran derivatives, thiophene derivatives and benzothiophene derivatives, optionally comprising nitrogen-containing substituents, such as those described in the documents U.S. Pat. No. 4,931,459, U.S. Pat. No. 4,910,317 and EP-A-299457, and more especially alkoxy- and/or aryloxy-tetrazol-yl-benzofuran-carboxamides or alkoxy- and/or aryloxy-tetrazol-yl-benzothiophene-carboxamides. By way of example, there may be mentioned 5-methoxy-3-phenoxy-N-1H-tetrazol-5-yl-benzothiophene-2-carboxamide, 5-methoxy-3-(1-methylethoxy)-N-1H-tetrazol-5-yl-benzothiophene-2-carboxamide, 6-methoxy-3-(1-methylethoxy)-N-1H-tetrazol-5-yl-benzothiophene-2-carboxamide, 5-methoxy-3-(1-methylethyl)-N-1H-tetrazol-5-yl-benzothiophene-2-carboxamide, 3-benzyloxy-5-methoxy-N-1H-tetrazol-5-yl-benzothiophene-2-carboxamide, and 5-methoxy-3-phenoxy-N-1H-tetrazol-5-yl-benzothiophene-2-carboxamide.

Among the antagonists of cytokines, there may be mentioned for example an antagonist of the release of interleukin-1 which can be used in the invention, which may be auranofin or SKF-105809 or alternatively an antagonist of the synthesis of interleukin-1 which may be lactoferin.

The receptor antagonists of TNF-a and the inhibitors of the release and/or of the synthesis of TNF-a which can be used in the invention are in particular lisophyline, A802715, sulfasalazine.

The antagonists of histamine, cytokines and TNF-a may be synthesized or extracted from naturally occurring products (plants or animals).

The antagonists of histamine, cytokines and TNF-a may be used according to the invention, separately or combined, alone or in the form of a mixture.

The quantity of compound reducing the synthesis, release and/or activity of at least one inflammation mediator, contained in the composition of the invention of course depends on the desired effect and may therefore vary to a large extent.

To give an order of magnitude, the cosmetic composition of the invention may contain a compound reducing the synthesis, release and/or activity of at least one inflammation mediator in a quantity representing from 0.001% to 5% of the total weight of the composition and preferably in a quantity representing from 0.01% to 2% of the total weight of the composition.

To give an order of magnitude, the pharmaceutical composition of the invention may contain a compound reducing the synthesis, release and/or activity of at least one inflammation mediator in a quantity representing from 0.001% to 10% of the total weight of the composition and preferably in a quantity representing from 0.01% to 5% of the total weight of the composition.

Regardless of the form of the composition according to the invention, the quantity of extract of at least one Iridaceae contained in the composition of course depends on the desired effect and may therefore vary to a large extent.

To give an order of magnitude, if the composition is a cosmetic composition it may contain an extract of at least one Iridaceae in a quantity representing from 0.001% to 20% of the total weight of the composition and preferably in a quantity representing from 0.1% to 10% of the total weight of the composition.

To give an order of magnitude, if the composition is a pharmaceutical composition, it may contain an extract of at least one Iridaceae in a quantity representing from 0.1% to 30% of the total weight of the composition and preferably in a quantity representing from 0.5% to 20% of the total weight of the omposition.

The composition according to the invention may be ingested, injected or applied to the skin (over any skin region of the body), the hair, the nails or the mucous membranes (buccal, jugal, gingival, genital, conjunctiva). Depending on the mode of administration, the composition according to the invention may be provided in any of the galenic forms normally used.

For a topical application to the skin, the composition may be especially in the form of an aqueous or oily solution or of a dispersion of the lotion or serum type, of emulsions of liquid or semiliquid consistency of the milk type, which are obtained by dispersing a fatty phase in an aqueous phase (O/W) or conversely (W/O), or of suspensions or emulsions of soft consistency of the aqueous or anhydrous cream or gel type, or alternatively of microcapsules or microparticles, or of vesicular dispersions of the ionic and/or nonionic type. These compositions are prepared according to the customary methods.

They may also be used for the hair in the form of aqueous, alcoholic or aqueous-alcoholic solutions, or in the form of creams, gels, emulsions, foams or alternatively in the form of compositions for aerosol also comprising a pressurized propelling agent.

For injection, the composition may be provided in the form of an aqueous or oily lotion or in the form of a serum. For the eyes, it may be provided in the form of drops, and for ingestion, it may be provided in the form of capsules, granulates or syrups or tablets.

The quantities of the various constituents of the compositions according to the invention are those conventionally used in the domains considered.

These compositions constitute especially creams for cleansing, protecting, treating or caring for the face, for the hands, for the feet, for the large anatomical skin-folds or for the body, (for example day creams, night creams, make-up removing creams, foundation creams, antisun creams), fluid foundations, make-up removing milks, body protecting or care milks, antisun milks, skin care lotions, gels or foams, such as cleansing lotions, antisun lotions, artificial tanning lotions, bath compositions, deodorant compositions comprising a bactericidal agent, aftershave gels or lotions, depilatory creams, compositions against insect bites, antipain compositions, compositions for treating certain skin diseases such as eczema, rosacea, psoriasis, lichens, severe pruritus.

The compositions according to the invention may also consist of solid preparations constituting cleansing cakes or soaps.

The compositions may be also packaged in the form of a composition for aerosol also comprising a pressurized propelling agent.

The composition according to the invention may also be a composition for hair care, and especially a shampoo, a hair setting lotion, a treatment lotion, a hair styling gel or cream, a dyeing composition (especially oxidation dyes) optionally in the form of colouring shampoos, restructuring lotions for the hair, a permanent-waving composition (especially a composition for the first stage of a permanent waving), a lotion or gel for preventing hair loss, an antiparasitic shampoo and the like.

The composition may also be for dentibuccal use, for example a toothpaste. In this case, the composition may contain customary adjuvants and additives for compositions for buccal use and especially surfactants, thickeners, humectants, polishing agents such as silica, various active ingredients such as fluorides, in particular sodium fluoride, and optionally sweeteners such as sodium saccharinate.

When the composition is an emulsion, the proportion of the fatty phase may range from 5% to 80% by weight, and preferably from 5% to 50% by weight relative to the total weight of the composition. The oils, waxes, emulsifiers and coemulsifiers used in the composition in the form of an emulsion are chosen from those conventionally used in the cosmetic field.

The emulsifier and coemulsifier are present in the composition in a proportion ranging from 0.3% to 30% by weight, and preferably from 0.5 to 20% by weight relative to the total weight of the composition. The emulsion may, in addition, contain lipid vesicles.

When the composition is an oily gel or solution, the fatty phase may represent more than 90% of the total weight of the composition.

In a known manner, the cosmetic composition may also contain usual adjuvants in the cosmetic field, such as hydrophilic or lipophilic gelling agents, hydrophilic or lipophilic additives, preservatives, anti-oxidants, solvents, perfumes, fillers, screening agents, odour absorbers and colouring matter. The quantities of these various adjuvants are those conventionally used in the cosmetic field, and are for example from 0.01% to 10% of the total weight of the composition. These adjuvants, depending on their nature, may be introduced into the fatty phase, into the aqueous phase and/or into the lipid spherules.

As oils or waxes which may be used in the invention, there may be mentioned mineral oils (petroleum jelly), vegetable oils (liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin. Fatty alcohols and fatty acids (stearic acid) may be added to these oils.

As emulsifiers which may be used in the invention, there may be mentioned for example glycerol stearate, polysorbate 60 and PEG-6/PEG-32/Glycol Stearate mixture sold under the name Tefose® 63 by the company Gattefosse.

As solvents which may be used in the invention, there may be mentioned lower alcohols, especially ethanol and isopropanol, propylene glycol.

As hydrophilic gelling agents which may be used in the invention, there may be mentioned carboxyvinyl polymers (carbomer), acrylic copolymers such as acrylate/alkylacrylate copolymers, polyacrylamides, polysaccharides such as hydroxypropyl cellulose, naturally occurring gums and clays, and, as lipophilic gelling agents, there may be mentioned modified clays such as bentones, metal salts of fatty acids such as aluminium stearates and hydrophobic silica, ethyl cellulose, polyethylene.

The composition may contain other hydrophilic active agents such as proteins or protein hydrolysates, amino acids, polyols, urea, allantoin, sugars and sugar derivatives, water-soluble vitamins, plant extracts and hydroxy acids.

As lipophilic active agents, it is possible to use retinol (vitamin A) and its derivatives, tocopherol (vitamin E) and its derivatives, essential fatty acids, ceramides, essential oils, salicylic acid and its derivatives.

According to the invention, the composition may combine at least one extract of at least one Iridaceae with other active agents intended especially for the prevention and/or treatment of skin conditions. Among these active agents, there may be mentioned by way of example:

agents modulating skin pigmentation and/or proliferation and/or differentiation such as retinoic acid and its isomers, retinol and its esters, vitamin D and its derivatives, oestrogens such as oestradiol, kojic acid or hydroquinone;

antibacterial agents such as clindamycin phosphate, erythromycin or antibiotics in the class of tetracyclins;

antiparasitic agents, in particular metronidazole, crotamiton or pyrethrinoids;

antifungal agents, in particular the compounds belonging to the class of imidazoles such as econazole, ketoconazole or miconazole or their salts, polyene compounds, such as amphotericin B, compounds of the family of allylamines, such as terbinafin, or alternatively octopirox;

antiviral agents such as acyclovir;

steroidal anti-inflammatory agents, such as hydrocortisone, betamethasone valerate, clobetasol propionate, or nonsteroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruriginous agents such as thenaldine, trimeprazine or cycloheptadine;

keratolytic agents such as alpha- and beta- hydroxycarboxylic or beta-ketocarboxylic acids, their salts, amides or esters and more particularly hydroxy acids such as glycolic acid, lactic acid, salicylic acid, citric acid and in general fruit acids, and n-octanoyl-5-salicylic acid;

anti-free radical agents, such as alpha-tocopherol or its esters, superoxide dismutases, some metal chelators or ascorbic acid and its esters;

antiseborrhoeic agents such as progesterone;

antidandruff agents such as octopirox or zinc pyrithione;

antiacne agents such as retinoic acid or benzoyl peroxide.

Thus, according to a specific embodiment, the invention relates to a composition containing at least one extract of at least one Iridaceae and at least one agent chosen from antibacterial, antiparasitic, antifungal, antiviral, anti-inflammatory, antipruriginous, anaesthetic, keratolytic, anti-free radical, antiseborrhoeic, antidandruff and antiacne agents and/or agents modulating skin pigmentation and/or proliferation and/or differentiation.

The subject of the invention is, in addition, a process of cosmetic treatment intended to reduce the irritant effect of a cosmetic composition, characterized in that a cosmetic composition as described above is applied to the skin, the hair and/or the mucous membranes.

The process of cosmetic treatment of the invention may be carried out especially by applying the hygiene or cosmetic compositions as defined above, according to the usual technique for using these compositions. For example: application of creams, gels, serums, lotions, make-up removing milks or antisun compositions to the skin or to dry hair, application of a lotion for the hair to wet hair, of shampoos, or alternatively application of toothpaste to the gums.

The following examples of compositions illustrate the invention without limiting it in any manner. In the compositions, the proportions indicated are percentages by weight.

EXAMPLE 1

Preparation of an Extract of *Iris pallida*

Undifferentiated cells of *Iris pallida* obtained by in vitro cultures under axenic conditions are recovered after culture in an Erlenmeyer flask or in a fermenter by filtration on a 50 mm sieve. 27.5 ml of demineralized water are added to 55 g of fresh material thus obtained. The mixture is ground (Potter, Ultra Turax and the like) in a Turax at 24,000 rpm for 1 minute at 4° C. (ice bath). The ground product is centrifuged for 15 min at 10,000 g at 4° C. The supernatant is filtered at 0.22 mm (sterilizing filtration).

The extract thus prepared is stored at 4° C. It contains about 15 g of dry matter per litre.

If the plant material is whole plant, the fresh material to be treated is expressed in terms of the dry weight in order to be under the same extraction conditions as in vitro. The various parts of the plant are removed according to the relative weight of each part thereof. The cold treatment makes it possible to gel the enzymatic activities, the sterilizing filtration avoids the degradation of the active ingredients by microorganisms in the environment. Finally, the water vehicle is compatible with the receptors ex vivo and facilitates the cosmetic or pharmaceutical formulations.

EXAMPLE 2

Measurement of the Receptor Affinity of the Extract of Undifferentiated Cells of *Iris pallida* (Example 1) for the Human NK1 Receptor (Human Substance P Receptor)

A): Receptor Affinity:

The measurement of the receptor affinity of the extract of undifferentiated cells of *Iris pallida* for the human NK1 receptor was carried out according to the method described in the article: Heuillet, E. et. al., J. Neurochem. 60, 1993, 868–876.

The extract is tested at the concentrations of 1%, 5% and 10%.

During each experiment, the reference molecule for the receptor studied ([Sar$^9$, Met (O$_2$)$^{11}$]-SP, substance P analogue described by Heuillet, E. (Heuillet, E. et al., J. Neurochem. 60, 1993, 868–876)) is tested in parallel at 8 concentrations (n=2) in order to obtain a standard curve which makes it possible to validate the experiment.

There are thus Obtained:

26.8% attachment for the extract of Example 1 at 1%

43.5% attachment for the extract of Example 1 at 5%

89.3% attachment for the extract of Example 1 at 10%

The results of this experiment demonstrate an affinity of the extract of undifferentiated cells of *Iris pallida* for the human substance P receptor starting from the concentration of 1%.

The affinity curve plotted according to the results obtained shows a 50% displacement of the natural ligand (IC50) by the *Iris pallida* extract at the concentration of 2%.

B): Functional Test In Vitro:

A functional test in vitro carried out on the human NK1 receptor (human substance P receptor) present on the smooth muscles of an isolated intestine (ileum) is carried out in order to demonstrate the substance P-antagonizing character of the extract of undifferentiated cells of *Iris pallida*.

The in vitro experiments were carried out according to the method described by Dion et al. (Life Sciences, 41, 1987, 2269–2278) and Patacchini et al. (Eur. J. Pharmacol., 215, 1992, 93–98).

After establishment in experimental tanks, the tissues (smooth muscles) are subjected to an initial tension of 1 g. An equilibration period of at least 60 minutes, during which the physiological solution is replaced several times and the initial tension readjusted, is then observed before adding the extract.

The experiments are performed in the continuous presence of atropine ($3'10^{-6}$ M), of pyrilamine ($3'10^{-6}$ M) and of indometacin ($10^{-6}$ M) in order to eliminate the indirect effects of mediators used during the stimulation of other types of receptors present on this tissue.

Each preparation is initially stimulated by a substance P agonist: [Sar$^9$, Met (O$_2$)$^{11}$]-SP, at the concentration of $10^{-8}$ M in order to obtain a "control" contractile response, and then the physiological solution is completely renewed.

This operation is then repeated every 40 minutes in the presence of increasing concentrations of the *Iris pallida* extract, each of them being added 30 minutes before the [Sar$^9$, Met (O$_2$)$^{11}$]-SP.

A 50% inhibition of the activity of [Sar$^9$, Met (O$_2$)$^{11}$]-SP is obtained at the extract concentration of 7%.

C): Functional Test In Vivo:

A functional test in vivo is carried out on a neurogenic inflammation model in order to demonstrate the substance P-antagonizing character of the *Iris pallida* extract (Example 1).

The in vivo experiments are carried out according to the method described by Xu, X.J. et al., (Neurosciences, 1991, 42, 731–737).

The test consists in causing an inflammation by the antidromic stimulation of the saphenous nerve in an anaesthetized animal. This nerve innervates the skin areas of the hind legs.

The stimulation causes the release, from the nerve endings, of substance P, responsible in part for the neurogenic inflammation.

The neurogenic inflammation is quantified by measuring the tissue permeability to Evans blue, a marker of tissue extravasation of plasma albumin which occurs during the inflammation.

This reference model is used for the in vivo test for substance P antagonists.

The *Iris pallida* extract, in its aqueous form, administered diluted 1/10, causes a statistically significant reduction of 38% in the neurogenic inflammation.

Conclusions:

The extract of undifferentiated cells of *Iris pallida* has an affinity for the receptor for substance P and exerts a substance P-antagonizing specific activity.

EXAMPLE 3

Measurement of the receptor affinity of the extract of undifferentiated cells of *Iris pallida* (Example 1) for the CGRP receptor.

A): Receptor Affinity:

The measurement of the receptor affinity of the extract of undifferentiated cells of *Iris pallida* of Example 1 for the CGRP receptor was carried out according to the method described in the article: Mimeault, M. et. al., J. Med. Chem. 35, 1992, 2163–2168.

The extract is tested at the concentrations of 0.5%, 1% and 5%.

During each experiment, the reference molecule for the receptor studied (the compound hCGRPa, analogue of CGRP described by Mimeault M. (Mimeault, M. et al., J. Med. Chem., 35, 1992, 2163–2168)) is tested in parallel at 8 concentrations (n=2) in order to obtain a standard curve which makes it possible to validate the experiment.

There are thus Obtained:

17% attachment for the extract of Example 1 at 0.5%

36% attachment for the extract of Example 1 at 1%

100% attachment for the extract of Example 1 at 5%

The results of this experiment demonstrate an affinity of the extract of undifferentiated cells of *Iris pallida* for the human CGRP receptor starting from the concentration of 0.5%.

The affinity curve plotted based on the results obtained shows a 50% displacement of the natural ligand (IC50) by the *Iris pallida* extract at the concentration of 2.5%.

B): Functional Test In Vitro:

A functional test in vitro carried out on the CGRP receptors present on the smooth muscles of the vas deferens is carried out in order to demonstrate the CGRP-antagonizing character of the *Iris pallida* extract.

The experiments ex vivo are carried out according to the method described by Longmore et al. (Eur. J. Pharmacol., 265, 1994, 53–59).

After establishment in experimental tanks, the tissues (smooth muscles) are subjected to an initial tension of 1 g. An equilibration period of at least 60 minutes, during which the physiological solution is replaced several times and the initial tension readjusted, is then observed.

Following this period, an electrical stimulus is applied to the smooth muscle of the vas deferens, the extract is added after stabilization of the contractile response induced by this stimulus, that is to say about 30 minutes.

The experiments are performed in the continuous presence of thiorphan ($10^{-5}$ M) in order to inhibit the degradation of CGRP or of its analogues by the endopeptidases present in this tissue.

Each preparation is exposed to hCGRPa (analogue of CGRP) at the concentration of $10^{-8}$ M in order to obtain a control inhibitory response. After stabilization of this response, increasing concentrations of the *Iris pallida* extract or of hCGRPa, are tested cumulatively, a recovery in the contractions by these compounds indicating an antagonistic effect on the CGRP receptors.

The *Iris pallida* extract is tested at the following 3 concentrations: 0.5%, 1% and 5% of its initial concentration.

The results obtained are compared with those for the reference molecules. The number of preparations used in each case is 2 (n=2).

After prior inhibition of the contractions by hCGRPa, the *Iris pallida* extract allows a recovery of the latter, an effect which is qualitatively identical to that exerted by hCGRPa.

A 50% inhibition of the activity of hCGRPa is obtained at the extract concentration of 0.8%.

Conclusions:

The extract of undifferentiated cells of *Iris pallida* exhibits an affinity for the CGRP receptor and exerts a CGRP-antagonizing specific activity.

EXAMPLE 4

Examples of formulations illustrating the invention. These compositions were obtained simply by mixing the various components.

Composition 1: Make-up Removing Lotion for the Face
  Extract of Example 1 5.00
  Antioxidant 0.05
  Isopropanol 40.00
  Preservative 0.30
  Water qs 100%

Composition 2: Face Care Gel
  Extract of Example 1 0.50
  Hydroxypropyl cellulose (Klucel H sold by the company Hercules) 1.00
  Antioxidant 0.05
  Isopropanol 40.00
  Preservative 0.30
  Water qs 100%

Composition 3: Face Care Cream (Oil-in-water Emulsion)
  Extract of Example 1 2.00
  Glycerol stearate 2.00
  Polysorbate 60 (Tween 60 sold by the company ICI) 1.00
  Stearic acid 1.40
  Triethanolamine 0.70
  Carbomer 0.40
  Liquid fraction of shea butter 12.00
  Perhydrosqualene 12.00
  Antioxidant 0.05
  Perfume 0.50
  Preservative 0.30
  Water qs 100%

Composition 4: Shampoo
  Extract of Example 1 0.50
  Hydroxypropyl cellulose (Klucel H sold by the company Hercules) 1.00
  Perfume 0.50
  Preservative 0.30
  Water qs 100%

Composition 5: Antipain Gel
  Extract of Example 1 5.00
  Hydroxypropyl cellulose (Clucel H sold by the company Hercules) 1.00

Antioxidant 0.05
Lidocaine hydrochloride 2.00
Isopropanol 40.00
Preservative 0.30
Water qs 100%

Composition 6: Antiwrinkles Care Cream for the Face (Oil/water Emulsion)
Extract of Example 1 0.15
Glycerol stearate 2.00
Polysorbate 60 (Tween 60 sold by the company ICI) 1.00
Stearic acid 1.40
n-Octanoyl-5-salicylic acid 0.50
Triethanolamine 0.70
Carbomer 0.40
Liquid fraction of shea butter 12.00
Perhydrosqualene 12.00
Antioxidant 0.05
Perfume 0.5
Preservative 0.300
Water qs 100%

Composition 7: Solar Erythema Care Cream (Oil-in-water Emulsion)
Extract of Example 1 2.50
Glycerol stearate 2.00
Polysorbate 60 (Tween 60 sold by the company ICI) 1.00
Stearic acid 1.40
Glycyrrhetinic acid 2.00
Triethanolamine 0.70
Carbomer 0.40
Liquid fraction of shea butter 12.00
Sunflower oil 10.00
Antioxidant 0.05
Perfume 0.50
Preservative 0.30
Water qs 100%

Composition 8: Gel for the Treatment of Acne
Extract of Example 1 5.00
All-trans-retinoic acid 0.05
Hydroxypropyl cellulose (Klucel H) 1.00
Antioxidant 0.05
Isopropanol 40.00
Preservative 0.30
Water qs 100%

Composition 9: Lotion for Removing Scars due to Acne
Extract of Example 1 5.00
Glycolic acid 50.00
Hydroxypropyl cellulose (Klucel H) 0.05
NaOH qs pH=2.8
Ethanol qs 100%
Preservative 0.30

Composition 10: Make-up Removing Lotion for the Face
Extract of Example 1 5.00
Strontium chloride 5.00
Antioxidant 0.05
Isopropanol 40.00
Preservative 0.30
Water qs 100%

Composition 11: Face Care Gel
Extract of Example 1 5.00
Vichy thermal water 10.00
Hydroxypropyl cellulose (Klucel H sold by the company Hercules) 1.00
Antioxidant 0.05
Isopropanol 40.00
Preservative 0.30
Water qs 100%

Composition 12: Face Care Cream (Oil-in-water Emulsion)
Extract of Example 1 5.00
Auranofin 0.10
Glycerol stearate 2.00
Polysorbate 60 (Tween 60 sold by the company ICI) 1.00
Stearic acid 1.40
Triethanolamine 0.70
Carbomer 0.40
Liquid fraction of shea butter 12.00
Perhydrosqualene 12.00
Antioxidant 0.05
Preservative 0.30
Water qs 100%

Composition 13: Shampoo
Extract of Example 1 5.00
Strontium chloride 5.00
Hydroxypropyl cellulose (Klucel H sold by the company Hercules) 1.00
Perfume 0.50
Preservative 0.30
Water qs 100%

Composition 14: Lotion for Removing Scars due to Acne
Extract of Example 1 5.00
HOE 140 0.05
Glycolic acid 50.00
Hydroxypropyl cellulose (Klucel H sold by the company Hercules) 0.05
NaOH qs pH=2.8
Ethanol qs 100%
Preservative 0.30

Composition 15: Solar Erythema Care Cream (Oil-in-water Emulsion)
Extract of Example 1 5.00
Vichy thermal water 10.00
Glycerol stearate 2.00
Polysorbate 60 (Tween 60 sold by the company ICI) 1.00
Stearic acid 1.40
Glycyrrhetinic acid 2.00
Triethanolamine 0.70
Carbomer 0.40
Liquid fraction of shea butter 12.00
Sunflower oil 10.00
Antioxidant 0.05
Perfume 0.50
Preservative 0.30
Water qs 100%

Composition 16: Gel for the Treatment of Acne
Extract of Example 1 5.00
CGRP 8–35 0.50

All-trans-retinoic acid 0.05
Hydroxypropyl cellulose (Klucel H sold by the company Hercules) 1.00
Antioxidant 0.05
Isopropanol 40.00
Preservative 0.30
Water qs 100%

Composition 17: Anti-pain Gel

Extract of Example 1 5.00

Carbomer 0.40
Liquid fraction of shea butter 12.00
Perhydrosqualene 12.00
Antioxidant 0.05
Perfume 0.50
Preservative 0.30
Water qs 100%

SEQUENCE LISTING

<160> NUMBER OF SEQ ID NOS: 1

<210> SEQ ID NO 1
<211> LENGTH: 11
<212> TYPE: PRT
<213> ORGANISM: Iris pallida
<220> FEATURE:
<221> NAME/KEY: PEPTIDE
<222> LOCATION: (1)..(2)
<223> OTHER INFORMATION: Amino acid 1 is Xaa wherein Xaa = D-NicLys
      which is D-lysine nicotinate.
<220> FEATURE:
<221> NAME/KEY: PEPTIDE
<222> LOCATION: (3)..(4)
<223> OTHER INFORMATION: Amino acid 3 is Xaa wherein Xaa = 3-Pal which
      is 3-pyridyl-alanine.
<220> FEATURE:
<221> NAME/KEY: PEPTIDE
<222> LOCATION: (5)..(6)
<223> OTHER INFORMATION: Amino acid 5 is Xaa wherein Xaa = D-Cl2Phe
      which is D-dichlorophenylalanine.
<220> FEATURE:
<221> NAME/KEY: PEPTIDE
<222> LOCATION: (7)..(9)
<223> OTHER INFORMATION: Amino acids 7 and 9 are Xaa wherein Xaa = D-Trp
      which is D-tryptophan.
<220> FEATURE:
<221> NAME/KEY: PEPTIDE
<222> LOCATION: (10)..(11)
<223> OTHER INFORMATION: Amino acid 11 is Xaa wherein Xaa = Nle which is
      norleucine.

<400> SEQUENCE: 1

Xaa Pro Xaa Pro Xaa Asn Xaa Phe Xaa Leu Xaa
 1               5                   10

Spantide II 0.05
Hydroxypropyl cellulose (Klucel H sold by the company Hercules) 1.00
Antioxidant 0.05
Lidocaine hydrochloride 2.00
Isopropanol 40.00
Preservative 0.30
Water qs 100%

Composition 18: Antiwrinkles Care Cream for the Face (Oil/water Emulsion)

Extract of Example 1 5.00
Lactoferin 1.00
Glycerol stearate 2.00
Polysorbate 60 (Tween 60 sold by the company ICI) 1.00
Stearic acid 1.40
n-Octanoyl-5-salicylic acid 0.50
Triethanolamine 0.70

What is claimed is:

1. Extract of root, stem, or leaf cells of at least one plant of the Iridaceae family, said plant being obtained by in vitro culture, which extract of cells upon topical application antagonizes at least one biological effect of substance P or calcitonin gene related peptide (CGRP).

2. Extract according to claim 1, characterized in that the cells are cells obtained from an Iridaceae of a genus selected from the group consisting of Romulea, Crocus, Iris, Gladiolus, Sisyrinchium and Hermodactylus.

3. Extract according to claim 2, wherein the said extract is an extract of plant material obtained from Iris.

4. Extract according to claim 3, wherein said extract is an extract of plant material obtained from *Iris pallida*.

5. Cosmetic orpharmaceutical composition which comprises, in a cosmetically or pharmaceutically acceptable medium, as an active ingredient, at least one extract of plant material as defined in claim 1.

6. Cosmetic orpharmaceutical composition, which comprises, in a cosmetically or pharmaceutically acceptable medium, an extract of cells of at least one plant of the Iridaceae family and at least one irritant.

7. Composition according to claim 6, wherein the irritant product is selected from the group consisting of ionic or nonionic surfactants, preservatives, organic solvents or active agents retinoids, selected from the group consisting of α-hydroxy acids, β-hydroxy acids, α-keto acids, β-keto acids, anthralins, anthranoids, peroxides, minoxidil, lithium salts, antimetabolites, vitamin D hair colorants or dyes, perfuming alcoholic solutions, antiperspirant agents, depilatory active agents, active agents for permanent waving, and depigmenting active agents.

8. Cosmetic orpharmaceutical composition, which comprises, in a cosmetically or pharmaceutically acceptable medium, an extract of cells of at least one plant of the Iridaceae family and a compound that reduces the synthesis, release and/or activity of at least one inflammation mediator.

9. Composition according to claim 6, wherein the extract of cells of at least one plant of the Iridaceae family is an extract of cells obtained by in vitro culture of at least one plant of the Iridaceae family.

10. Composition according to claim 8, wherein the compound that reduces the synthesis, release and/or activity of at least one inflammation mediator is a compound that reduces the synthesis, release and/or activity of at least one skin inflammation mediator.

11. Composition according to claim 8, wherein the compound that reduces the synthesis, release and/or activity of at least one inflammation mediator is chosen from antagonists of substance P and/or CGRP, inhibitors of NO-synthase, antagonists of bradykinin, antagonists of cytokines, antagonists of histamine, and antagonists of type a tumour necrosis factor (TNF a).

12. Composition according to claim 11, wherein said antagonists are receptor antagonists.

13. Composition according to claim 12, wherein said substance P antagonist is selected from the group consisting of substances which reduce the extravasation of plasma across the vascular wall induced by capsaicin or by an antidromic nerve stimulation, and substances which cause an inhibition of the contraction of the smooth muscles induced by the administration of substance P.

14. Composition according to claim 11, wherein said substance P antagonist is selected from the group consisting of peptides; compounds comprising at least one heterocycle; nitrogen-containing compounds comprising at least one benzene ring; salts of monovalent, divalent and trivalent cations; thermal waters; and mixtures thereof.

15. Composition according to claim 14, wherein said peptide is Sendide or Spantide II.

16. Composition according to claim 14, wherein said compound comprising at least one heterocycle is a nitrogen-, oxygen- or sulphur-containing heterocyclic compound selected from the group consisting of 2-tricyclyl-2-aminoethane compounds, spirolactam compounds, quinuclidine compounds, azacyclic compounds, aminopyrrolidine compounds, piperidine compounds, aminoazaheterocycles, isoindole compounds, furan compounds, benzofuran compounds, thiophene compounds, and benzothiophene compounds.

17. Composition according to claim 14, wherein said salt is selected from the group consisting of chlorides, acetates, carbonates, bicarbonates, salicylates, borates, nitrates, hydroxides, sulphates, persulphates, glycerophosphates, salts of a-hydroxy acids, salts of fruit acids, salts of amino acids and salts of fatty acids, of strontium, magnesium, lanthanides of atomic number ranging from 57 to 71, cobalt, nickel, manganese, barium, yttrium, copper, tin, rubidium, lithium and zinc.

18. Composition according to claim 17, wherein said salt is a strontium salt.

19. Composition according to claim 17, wherein said salt is strontium chloride or nitrate.

20. Composition according to claim 14, wherein said thermal water is obtained from a spring from the Vichy basin.

21. Composition according to claim 20, wherein said thermal water is obtained from the Celestins, Chomel, Grande-Grille, Hôpital, Lucas or Parc springs of the Vichy basin.

22. Composition according to claim 20, wherein said thermal water is obtained from the Lucas spring.

23. Composition according to claim 11, wherein said CGRP antagonist is selected from the group consisting of substances which reduce vasodilation induced by capsaicin or antidromic electric stimulus; substances which inhibit the release of CGRP by sensitive nerve fibers; and substances which inhibit the contraction of smooth muscle of the vas deferens induced by CGRP.

24. Composition according to claim 23, wherein said CGRP antagonist is selected from the group consisting of CGRP 8–37 and anti-CGRP antibodies.

25. Composition according to claim 11, wherein said inhibitor of NO-synthase is a substance which inhibits the synthesis of nitrogen monoxide in vivo.

26. Composition according to claim 25, wherein said inhibitor of NO-synthase is selected from the group consisting of compounds that inhibit the synthesis or accelerate the catabolism of NO-synthase; compounds that neutralize NO-synthase; and compounds that reduce the signal transduced by NO-synthase.

27. Composition according to claim 25, wherein said inhibitor of NO-synthase is a chemical molecule that inhibits the synthesis of nitrogen monoxide.

28. Composition according to claim 25, wherein said inhibitor of NO-synthase is selected from the group consisting of $N^G$-monomethyl-L-arginine (L-NMMA), $N^G$-nitro-L-arginine, the methylated ester of $N^G$-nitro-L-arginine, diphenyleneiodonium chloride, 7-nitroindazole, N(5)-(1-iminoethyl)-L-ornithine, $N^G,N^G$-dimethyl-L-arginine, $N^G,N^G$-dimethylarginine, 2-(4-carboxyphenyl)-4,4,5,5-tetramethylimidazoline-1-oxy-3-oxide, ebselen, aminoguanidine, canavanine, and type a melanocyte-stimulating hormone.

29. Composition according to claim 25, wherein said inhibitor of NO-synthase is $N^G$-monomethyl-L-arginine or type a melanocyte-stimulating hormone.

30. Composition according to claim 11, wherein said bradykinin antagonist is selected from the group consisting of compounds that inhibit the synthesis or accelerate the catabolism of bradykinin, compounds that neutralize bradykinin, compounds that block bradykinin receptors, compounds that inhibit the synthesis of the receptors for bradykinin and compounds which decrease the signal transduced by bradykinin.

31. Composition according to claim 30, wherein said bradykinin antagonist is a chemical molecule that inhibits the biological effect of bradykinin.

32. Composition according to claim 30, wherein said bradykinin antagonist is a compound which interferes with the effects of bradykinin by its attachment to the B1 or B2 receptor.

33. Composition according to claim 30, wherein said bradykinin antagonist is selected from the group consisting of D-Arg, [Hyp3, D-Phe7]-bradykinin (NPC567), [Thi 5, 8, D-Phe7]-bradykinin, D-Arg, [Hyp3, Thi5,8, D-Phe7]- bradykinin, N-a-adamantaneacetyl-D-Arg, [Hyp3, Thi5,8, D-Phe7]-bradykinin, des-Arg9, [Leu8]-bradykinin, P-guanidobenzoyl-[Hyp3, Thi5, D-Tic7, Oic8]-bradykinin (S 16118), D-Arg, [Hyp3, Thi5, D-Tic7, Oic8]-bradykinin (HOE 110), and D-Arg, [Hyp3, D-Hype (trans-propyl)7 Oic8]-bradykinin (NPC 13731).

34. Composition according to claim 30, wherein said bradykinin antagonist is D-Arg, [Hyp3, Thi5, D-Tic7, Oic8]-bradykinin (HOE 110).

35. Composition according to claim 11, wherein said antagonist of histamine, cytokines or TNF-α is a substance selected from the group consisting of substances that antagonize the receptors of histamine, cytokines or TNF-α; and substances that antagonize the release or synthesis of histamine, cytokines or TNF-α.

36. Composition according to claim 35, wherein said antagonist substance is selected from the group consisting of receptor antagonists of histamine, cytokines or TNF-α having a selective affinity for the specific receptors for these compounds; substances which inhibit the contraction of smooth muscles induced by the administration of histamine; substances which inhibit the adhesion of macrophages induced by cytokines on endothelial cells; substances which inhibit the release of superoxide anions induced by cytokines on neutrophils; substances which inhibit the adhesion of macrophages induced by TNF-α on endothelial cells; and substances which inhibit the release of superoxide anions induced by TNF-α on neutrophils or which inhibit the mitogenic activity of TNF-α on fibroblasts of the dermis.

37. Composition according to claim 35, wherein said receptor antagonist of histamine is selected from the group consisting of diethylenediamine compounds aminopropane compounds and phenothiazine compounds.

38. Composition according to claim 35, wherein said antagonist of the release of histamine is selected from the group consisting of oxygen-containing or sulphur-containing heterocyclic compounds.

39. Composition according to claim 35, wherein said antagonist of the release of histamine is selected from the group consisting of 5-methoxy-3-phenoxy-N-1H-tetrazol-5-yl-benzothiophene-2-carboxamide, 5-methoxy-3-(1-methylethoxy)-N-1H-tetrazol-5-yl-benzothiophene-2-carboxamide, 6-methoxy-3-(1-methylethoxy)-N-1H-tetrazol-5-yl-benzothiophene-2-carboxamide, 5-methoxy-3-(1-methylethyl)-N-1H-tetrazol-5-yl-benzothiophene-2-carboxamide, 3-benzyloxy-5-methoxy-N-1H-tetrazol-5-yl-benzothiophene-2-carboxamide, and 5-methoxy-3-phenoxy-N-1H-tetrazol-5-yl-benzothiophene-2-carboxamide.

40. Composition according to claim 35, wherein said antagonist of cytokines is selected from the group consisting of antagonists of the release of interleukin-1 and antagonists of the synthesis of interleukin-1.

41. Composition according to claim 35, wherein said receptor antagonist of TNF-α said inhibitor of the release and/or synthesis of TNF-α is selected from the group consisting of lisophyline, A802715, and sulphasalazine.

42. Cosmetic composition according to claim 8, wherein the compound that reduces the synthesis, release and/or activity of at least one inflammation mediator is contained in a quantity representing from 0.001% to 5% of the total weight of the composition.

43. Pharmaceutical composition according to claim 8, wherein said compound which reduces the synthesis, release and/or activity of at least one inflammation mediator is contained in a quantity representing from 0.001% to 10% of the total weight of the composition.

44. Composition according to claim 8, which comprises, in addition, in a cosmetically or pharmaceutically acceptable medium, at least one irritant product.

45. Cosmetic composition according to claim 6 wherein said Iridaceae extract is used in a quantity representing from 0.001% to 20% of the total weight of the composition.

46. Pharmaceutical composition according to claim 5, wherein said Iridaceae extract is contained in a quantity representing from 0.1% to 30% of the total weight of the composition.

47. An improved method of therapy comprising the administration of CGRP antagonist or substance P antagonist, wherein the improvement comprises using as said antagonist at least one extract of cells of at least one plant of the Iridaceae family as antagonist of CGRP and/or substance P.

48. A method of treating at least a disorder associated with an excessive synthesis and/or release of CGRP and/or substance P, comprising administering to a host in need thereof an effective amount of an extract according to claim 1.

49. A method of treating a disorder selected from the group consisting of the central nervous system disorders, respiratory disorders, allergic syndromes, inflammation associated disorders, pain associated disorder, gastrointestinal disorders, skin disorders, fibrosis associated disorders, collagen maturation disorders, cardiovascular disorders, vasospastic disorders, immunological disorders, disorders of the urinary tract or a combination thereof, comprising administering to a host in need thereof an effective amount of an extract according to claim 1.

50. A method of treating sensitive skins, comprising administering an effective amount of an extract according to claim 1.

51. A method for treating skin disorders selected from the group consisting of skin irritations, dartres, erythemas, dysaesthetic sensations, sensations of inflammation, and pruritus of the skin or of the mucous membranes in a host in need of such treatment, comprising topically administering to said host an effective amount of an extract according to claim 1.

52. A method of cosmetic treatment wherein a cosmetic composition as defined in claim 5 is applied to the skin, the hair, or the mucous membranes, or a combination thereof, of a host in need of said treatment.

53. Composition according to claim 27, wherein said chemical molecule is selected from the group consisting of antisense nucleic acids, ribozymes, and anti-NO-synthase antibodies.

54. Composition according to claim 31, wherein said chemical molecule is selected from the group consisting of antisense nucleic acids, ribozymes, anti-bradykinin antibodies, soluble receptors for bradykinin, anti-bradykinin receptor antibodies and antagonists of bradykinin receptors.

55. Extract of undifferentiated cells of at least one plant of the Iridaceae family, said plant being obtained by in vitro culture, which extract of cells upon topical application antagonizes at least one biological effect of substance P or calcitonin gene related peptide (CGRP).

* * * * *